United States Patent
Brion et al.

(10) Patent No.: US 7,339,061 B2
(45) Date of Patent: Mar. 4, 2008

(54) 3-(4-OXO-4H-CHROMEN-2-YL)-(1H)-QUINOLIN-4-ONE DERIVATIVES, METHOD FOR PREPARING SAME AND PHARMACEUTICAL COMPOSITIONS CONTAINING SAME

(75) Inventors: Jean-Daniel Brion, Saint Leu la Foret (FR); Lucien Israel, Paris (FR); Alain Le Ridant, Neuilly sur Seine (FR); Catherine Harpey, Paris (FR); Cherif Rabhi, Les Lilas (FR); El Bachir Kaloun, Cergy Saint Christophe (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 589 days.

(21) Appl. No.: 10/519,208

(22) PCT Filed: Jun. 18, 2003

(86) PCT No.: PCT/FR03/01849

§ 371 (c)(1),
(2), (4) Date: Dec. 17, 2004

(87) PCT Pub. No.: WO2004/000834

PCT Pub. Date: Dec. 31, 2004

(65) Prior Publication Data

US 2006/0063801 A1 Mar. 23, 2006

(30) Foreign Application Priority Data

Jun. 19, 2002 (FR) .................................. 02 07536

(51) Int. Cl.
C07D 215/38 (2006.01)

(52) U.S. Cl. ...................... 546/153; 546/157; 546/158

(58) Field of Classification Search ............... 546/153, 546/157, 158
See application file for complete search history.

(56) References Cited

OTHER PUBLICATIONS

Baczynski, CA 13L:12820, abstract only of Berichte der Deutschen Chemischen Gesellschaft, Abhandlungen, 52B, pp. 461-484, 1919.*

Chemical Abstracts, vol. 123, No. 5, 1995, p. 906, abstract # 55705x.
International Search Report; PCT/FR03/01849; Sep. 26, 2003.
International Preliminary Examination Report; PCT/FR03/01849; Jan. 14, 2004.
International Preliminary Examination Report for PCT/FR2003/001849, May 18, 2006.

* cited by examiner

*Primary Examiner*—D. Margaret Seaman
(74) *Attorney, Agent, or Firm*—Hueschen and Sage

(57) ABSTRACT

Compound of formula (I):

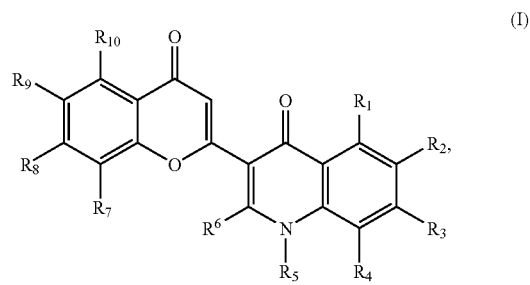

wherein:

$R_1$, $R_2$, $R_3$, $R_4$, $R_6$, $R_8$, $R_9$ and $R_{10}$, which may be the same or different, each represent a group selected from hydrogen, hydroxy, alkoxy, alkyl, arylalkoxy, alkoxycarbonylalkoxy and OR' wherein R' represents an ionised or ionisable group, $R_5$ represents a group selected from alkyl, aryl and heteroaryl, $R_7$ represents a group selected from hydrogen, hydroxy, alkoxy, alkyl and cycloalkyl, or $R_7$ represents a nitrogen-containing or oxygen-containing heterocycle, its optical isomers, hydrates and solvates thereof and addition salts thereof, with a pharmaceutically acceptable acid or base.

Medicinal products containing the same which are useful as anti-cancer agents.

12 Claims, No Drawings

3-(4-OXO-4H-CHROMEN-2-YL)-(1H)-QUINOLIN-4-ONE DERIVATIVES, METHOD FOR PREPARING SAME AND PHARMACEUTICAL COMPOSITIONS CONTAINING SAME

The present invention relates to new 3-(4-oxo-4H-chromen-2-yl)-(1H)-quinolin-4-one compounds, to a process for their preparation, to pharmaceutical compositions containing them and to their use as anti-cancer agents.

Anti-cancer therapeutic requirements call for the constant development of new anti-tumour agents with the aim of obtaining medicaments that are simultaneously more active and better tolerated.

Besides the fact that the compounds of the invention are new, they have very valuable anti-tumour properties.

On the one hand, they have a pro-apoptotic effect, an efficacy which is independent of the expression of p53, pRb and Bcl-2 and a marked anti-angiogenic effect and, on the other hand, they have synergy of action with a large number of cytostatic therapeutic agents without there being any additional haematotoxicity or, in general, any signs of intolerance.

As a result of those properties, the compounds of the invention are highly efficacious, well-tolerated adjuvants to chemotherapies and, at the same time, agents that are capable of maintaining and prolonging the effects of those chemotherapies when the latter are discontinued for various reasons: intolerance, finishing a course of treatment, discontinuation for reasons of surgery etc.

By virtue of their properties, the compounds of the invention can be advantageously associated with all cytotoxic treatments currently in use as well as with radiotherapies (without increasing the toxicity thereof) and the various hormonal therapies aimed at combatting cancers (breast and prostate).

More specifically, the present invention relates to compounds of formula (I):

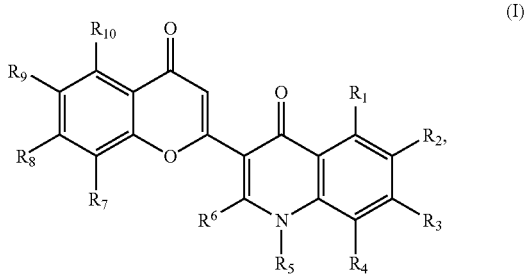

wherein:
$R_1$, $R_2$, $R_3$, $R_4$, $R_6$, $R_8$, $R_9$ and $R_{10}$, which may be the same or different, each represent a group selected from hydrogen, hydroxy, linear or branched ($C_1$-$C_6$)alkoxy, linear or branched ($C_1$-$C_6$)alkyl, arylalkoxy in which the alkoxy group is linear or branched ($C_1$-$C_6$), alkoxycarbonylalkoxy in which each of the alkoxy groups is linear or branched ($C_1$-$C_6$), and OR' wherein R' represents an ionised or ionisable group such as, for example, a phosphate group —PO(OH)$_2$, a sulfate group —SO$_3$H, carboxyalkylcarbonyl in which the alkyl group is linear or branched ($C_1$-$C_6$), dialkylaminoalkylcarbonyl in which each of the alkyl groups is linear or branched ($C_1$-$C_6$), or carboxyalkylaminocarbonyl in which the alkyl group is linear or branched ($C_1$-$C_6$), $R_5$ represents a group selected from linear or branched ($C_1$-$C_6$)alkyl, aryl and heteroaryl, $R_7$ represents a group selected from hydrogen, hydroxy, linear or branched ($C_1$-$C_6$)alkoxy, linear or branched ($C_1$-$C_6$)alkyl and ($C_3$-$C_7$)cycloalkyl, or $R_7$ represents a nitrogen-containing or oxygen-containing heterocycle, to optical isomers thereof when they exist, to addition salts thereof with a pharmaceutically acceptable acid and to hydrates and solvates thereof.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid.

An aryl group is understood to be phenyl, biphenylyl, naphthyl or tetrahydronaphthyl, each of those groups being optionally substituted by one or more identical or different atoms or groups selected from halogen atoms and linear or branched ($C_1$-$C_6$)alkyl groups, hydroxy groups, linear or branched ($C_1$-$C_6$)alkoxy groups, linear or branched ($C_1$-$C_6$) polyhaloalkyl groups, amino groups (optionally substituted by one or two linear or branched ($C_1$-$C_6$)alkyl groups), nitro groups and ($C_1$-$C_2$)alkylenedioxy groups.

A heteroaryl group is understood to be a 5- to 12-membered group which either is monocyclic and aromatic or is bicyclic with at least one of the rings being of aromatic character and which contains one, two or three hetero atoms selected from oxygen, nitrogen and sulphur, it being understood that the heteroaryl group may be optionally substituted by one or more identical or different atoms or groups selected from halogen atoms and linear or branched ($C_1$-$C_6$)alkyl groups, hydroxy groups, linear or branched ($C_1$-$C_6$)alkoxy groups, linear or branched ($C_1$-$C_6$)polyhaloalkyl groups and amino groups (optionally substituted by one or two linear or branched ($C_1$-$C_6$)alkyl groups). Among the heteroaryl groups there may be mentioned, without implying any limitation, thienyl, pyridyl, furyl, pyrrolyl, imidazolyl, oxazolyl, isoxazolyl, thiazolyl, isothiazolyl, quinolyl, isoquinolyl and pyrimidinyl groups.

A nitrogen-containing heterocycle is understood to mean a saturated or unsaturated, 5- to 7-membered monocyclic group containing a nitrogen atom and optionally substituted by one or more groups selected from hydroxy, linear or branched ($C_1$-$C_6$)alkoxy, linear or branched ($C_1$-$C_6$)alkyl, aryl-($C_1$-$C_6$)alkyl in which the alkyl moiety is linear or branched and amino-($C_1$-$C_6$)alkyl in which the alkyl moiety is linear or branched and in which the amino group is optionally substituted by one or two linear or branched ($C_1$-$C_6$)alkyl groups.

Nitrogen-containing heterocycles to which preference is given are optionally substituted piperidyl and tetrahydropyridyl groups.

An oxygen-containing heterocycle is understood to mean a saturated or unsaturated, 5- to 7-membered monocyclic group containing an oxygen atom and optionally substituted by one or more groups selected from hydroxy, linear or branched ($C_1$-$C_6$)alkoxy, linear or branched ($C_1$-$C_6$)alkyl, aryl-($C_1$-$C_6$)alkyl in which the alkyl moiety is linear or branched and amino-($C_1$-$C_6$)alkyl in which the alkyl moiety is linear or branched and in which the amino group is optionally substituted by one or two linear or branched $(C_1\text{-}C_6)$alkyl groups.

An advantageous aspect of the invention relates to compounds of formula (I) wherein $R_7$ represents an aryl group.

Another advantageous aspect of the invention relates to compounds of formula (I) wherein $R_7$ represents a hydrogen atom.

Another advantageous aspect of the invention relates to compounds of formula (I) wherein $R_7$ represents an optionally substituted nitrogen-containing heterocycle.

Preference is given to compounds of formula (I) wherein $R_5$ represents a phenyl group and $R_7$ represents a hydrogen atom or a substituted 1,2,3,6-tetrahydro-4-pyridyl group.

Among the preferred compounds of the invention there may be mentioned, more especially:

3-(5-hydroxy-4-oxo-4H-1-benzopyran-2-yl)-1-phenyl-1H-quinolin-4-one,

3-[5,7-dimethoxy-8-(1-methyl-1,2,5,6-tetrahydropyridin-4-yl)-4-oxo-4H-1-benzopyran-2-yl]-1-phenyl-1H-1,4-dihydroquinolin-4-one, 3-(5,7-dihydroxy-4-oxo-4H-1-benzopyran-2-yl)-1-phenyl-1H-1,4-dihydroquinolin-4-one and 3-[5,7-dihydroxy-8-(1-methyl-1,2,5,6-tetrahydropyridin-4-yl)-4-oxo-4H-1-benzopyran-2-yl]-1-phenyl-1H-1,4-dihydroquinolin-4-one.

The invention relates also to a process for the preparation of compounds of formula (I), which process is characterised in that a compound of formula (II):

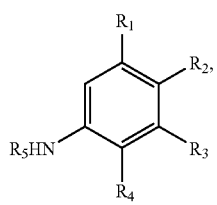

(II)

wherein $R_1$, $R_2$, $R_3$, $R_4$ and $R_5$ are as defined for formula (I), is reacted with diethyl ethoxymethylenemalonate to yield the compound of formula (III):

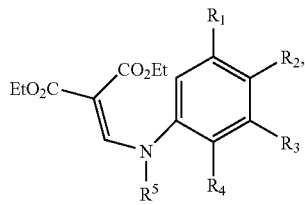

(III)

wherein $R_1$, $R_2$, $R_3$, $R_4$ and $R_5$ are as defined hereinbefore and Et represents an ethyl group, which is cyclised under acid conditions to yield the compound of formula (IV):

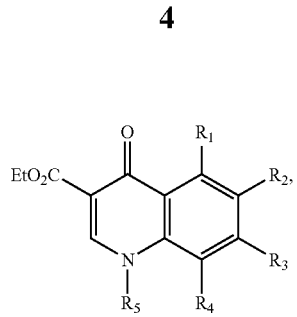

(IV)

wherein $R_1$, $R_2$, $R_3$, $R_4$ and $R_5$ and Et are as defined hereinbefore, which is hydrolysed to yield the compound of formula (V):

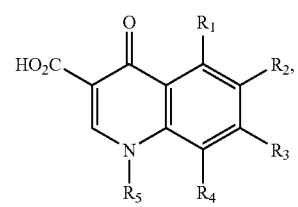

(V)

wherein $R_1$, $R_2$, $R_3$, $R_4$ and $R_5$ are as defined hereinbefore, which is converted by the action of thionyl chloride into an acid chloride, which is then reacted with the compound of formula (VI):

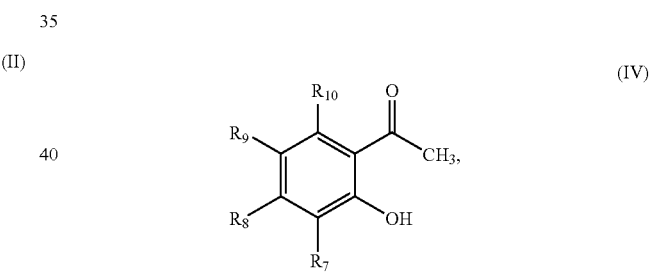

(IV)

wherein $R_7$, $R_8$, $R_9$ and $R_{10}$ are as defined for formula (I), to yield the compound of formula (VII):

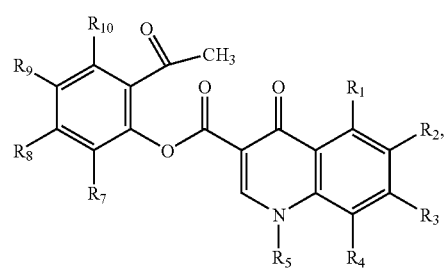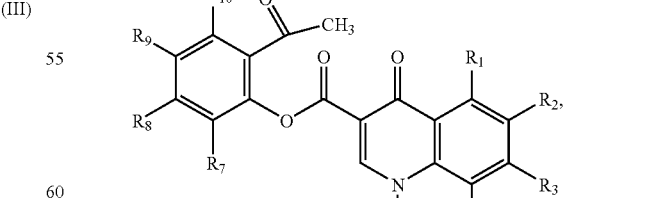

(VII)

wherein $R_1$, $R_2$, $R_3$, $R_4$, $R_5$, $R_6$, $R_7$, $R_8$, $R_9$ and $R_{10}$ are as defined hereinbefore, which is subjected to the action of a base to yield the compound of formula (VIII):

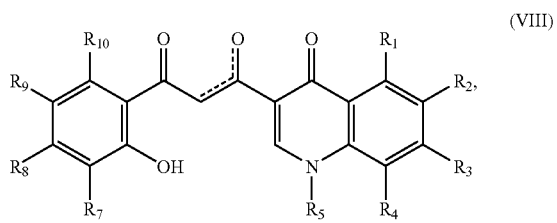

wherein $R_1$, $R_2$, $R_3$, $R_4$, $R_5$, $R_6$, $R_7$, $R_8$, $R_9$ and $R_{10}$ are as defined herinbefore, and

indicates that the compound is obtained, depending on the molecules involved, in the form of a keto-enol mixture, which is then subjected to acid conditions to yield the compound of formula (I), which is purified, if necessary, according to a conventional purification technique, which is separated, if necessary, into its optical isomers according to a conventional separation technique and which is converted, if desired, into its addition salts with a pharmaceutically acceptable acid.

Compounds of formula (I) wherein one or more of the substituents $R_1$ to $R_4$ and $R_6$ to $R_{10}$ represent(s) a hydroxy group may also be obtained by cleaving compounds of formula (I) wherein the corresponding substituent(s) represent(s) a linear or branched ($C_1$-$C_6$)alkoxy group.

Compounds of formula (I) wherein one or more of the substitutents $R_1$ to $R_4$ and $R_6$ to $R_{10}$ represent(s) an alkoxycarbonylalkoxy, arylalkoxy or OR' group may also be obtained starting from compounds of formula (I) wherein the corresponding substituent(s) represent(s) a hydroxy group.

Besides the fact that they are new, the compounds of the present invention have very valuable anti-tumour properties, making them of use in the treatment of cancers.

Among the types of cancer that may be treated by the compounds of the present invention, there may be mentioned, without implying any limitation, adenocarcinomas, carcinomas, sarcomas, gliomas and leukaemias.

They may also be used in therapeutic association with another anti-cancer agent such as, for example, paclitaxel, tamoxifen and its derivatives, cisplatin and its analogues, irinotecan and its metabolites, the various alkylating agents, the leading example of which is cyclophosphamide, etoposide, the vinca alkaloids, doxorubicin and other anthracyclines, and the nitrosoureas.

The invention relates also to pharmaceutical compositions comprising as active ingredient at least one compound of formula (I) together with one or more appropriate, inert, non-toxic excipients. Among the pharmaceutical compositions according to the invention there may be mentioned more especially those that are suitable for oral, parenteral (intravenous, intramuscular or sub-cutaneous) or nasal administration, tablets or dragées, sublingual tablets, capsules, lozenges, suppositories, creams, ointments, dermal gels, injectable preparations, drinkable suspensions etc.

The useful dosage can be adapted to the nature and severity of the disorder, the administration route, the age and weight of the patient and any associated treatments and ranges from 0.5 mg to 2 g per 24 hours in one or more administrations.

The following Examples illustrate the invention but do not limit it in any way.

The starting materials used are known products or are prepared according to known procedures.

The structures of the compounds described in the Examples were determined according to the usual spectrometric techniques (infrared, NMR, mass spectrometry).

EXAMPLE 1

3-(7-Methoxy-4-oxo-4H-1-benzopyran-2-yl)-1-phenyl-1H-1,4-dihydroquinolin-4-one

Step A: Diethyl N-N-diphenylaminomethylenemalonate 10 mmol of diethyl ethoxymethylenemalonate are added to 10 mmol of diphenylamine and the mixture is then heated at 140-150° C. for 5 hours. After returning to ambient temperature, the solid that is formed is rinsed with 100 mL of diethyl ether and recrystallised from hexane to yield the expected product in the form of a brown solid.

Melting point: 146-148° C.

MS (EI, m/z): 339.9 ($M^+$).

Step B: Ethyl 4-oxo-1-phenyl-1H-1,4-dihydroquinoline-3-carboxylate 13.3 g of polyphosphoric acid are added to 10 mmol of the compound obtained in the previous Step. The mixture (which gradually becomes liquid) is then heated at 150-160° C. for 45 minutes and is then cooled to 90° C. After hydrolysis, the mixture is neutralised using 10% NaOH solution to yield, after isolation, the expected product.

IR (NaCl plates, $cm^{-1}$): 1733 (vC=O), 1610 (vC=C), 1645 (vC=O), 690 (vC—H(ar)).

MS (EI, m/z): 293.3 ($M^+$).

Step C: 4-Oxo-1-phenyl-1H-1,4-dihydroquinoline-3-carboxylic acid:

To 10 mmol of the compound obtained in the previous Step, dissolved in methanol, there are added 38 mL of 2M NaOH solution. The reaction mixture is then heated at reflux of the methanol for 10 hours and the solvent is then removed in vacuo. Water is added to the residue obtained and the mixture is then neutralised with 4M HCl solution. The grey solid obtained is washed with water and then dried to yield the expected product.

Melting point: 210-213° C.

IR (KBr, $cm^{-1}$): 3320 (vOH(acid)), 1733 (vC=O), 1610 (vC=C), 1645 (vC=O), 690 (vC—H(ar)).

MS (EI, m/z): 265.3 ($M^+$).

Step D: (2-Acetyl-5-methoxy)phenyl 4-oxo-1-phenyl-1H-1,4-dihydroquinoline-3-carboxylate 10 mmol of the compound obtained in the previous Step are added to 20 mmol of thionyl chloride dissolved in dichloroethane. The reaction mixture is heated at reflux of the solvent for 2 hours and is then concentrated in vacuo, and the excess thionyl chloride is removed by distillation in vacuo with entrainment with dichloroethane, repeated several times.

The acid chloride thereby obtained (white solid) is added in small portions to 6.7 mmol of commercial 2-hydroxy-4-methoxyacetophenone dissolved in pyridine. After stirring for 12 hours under an inert atmosphere at ambient temperature, the reaction mixture is purified by chromatography on a silica column (eluant:$CH_2Cl_2$/MeOH:95/5) to yield the expected product in the form of a yellow powder.

Melting point: 137-139° C.

IR (KBr, $cm^{-1}$): 2865 ($vCH$ of $OCH_3$), 1740 ($vC=O$), 1655 ($vC=O$), 1590-1575 ($vC=C$).

MS (electrospray, m/z):413.4 ($M^+$).

Step E: 3-[3-(2-Hydroxy-4-methoxyphenyl)-1,3-dioxoprop-1-yl]-1H-1-phenyl-1,4-dihydroquinolin-4-one Under an inert atmosphere and at ambient temperature, 12 mmol of potassium tert-butanolate are slowly added to 10 mmol of the compound obtained in the previous Step, dissolved in a mixture of dimethylformamide and tetrahydrofuran (35/75). The reaction mixture is stirred for 2 hours and is then poured into a solution of 55 mL of water at 0° C. containing 1.3 mL of 10% hydrochloric acid. The precipitate obtained is filtered off, rinsed with copious amounts of water and then dried. The solid obtained is purified by chromatography on a silica column (eluant: $CH_2Cl_2$) to yield the expected product in the form of a keto-enol mixture.

Melting point: 228-230° C.

Step F: 3-(7-Methoxy-4-oxo-4H-1-benzopyran-2-yl)-1-phenyl-1H-1,4-dihydroquinolin-4-one To 10 mmol of the compound obtained in the previous Step, dissolved in 25 mL of glacial acetic acid, there are slowly added 25 mL of a solution of acetic acid containing 20% sulphuric acid. A yellow precipitate is formed. After 2 hours 30 minutes at ambient temperature, the mixture is poured into iced water (4° C.). The insoluble material is filtered off and rinsed with copious amounts of water to yield the expected product in the form of a white powder.

Melting point: 297° C.

IR ($cm^{-1}$): 2825 ($vOCH_3$), 1750 ($vC=O$), 1675 ($vC=O$), 1570-1590 ($vC=C$).

MS (electrospray, m/z): 396.1 ($M^+$).

Elemental Microanalysis:

|  | % C | % H | % N |
|---|---|---|---|
| Calculated: | 72.63 | 4.63 | 3.39 |
| Found | 72.46 | 4.57 | 3.27 |

EXAMPLE 2

3-(7-Hydroxy-4-oxo-4H-1-benzopyran-2-yl)-1-phenyl-1H-quinolin-4-one 10 mmol of the compound of Example 1 are added, with stirring, under an inert atmosphere and protected from light, to 500 mmol of phenol dissolved in 214 mL of hydriodic acid (57% aqueous solution). The heterogeneous reaction mixture is then heated at 160° C. for 15 hours. The initially yellow solution turns orange. After returning to ambient temperature, the solution is poured onto ice, and the precipitate obtained is rinsed with water and then with diethyl ether in order to remove the residual phenol, yielding, after recrystallisation, the expected product in the form of a yellow powder.

Melting point: 295-300° C. (acetone)

IR ($cm^{-1}$): 3280 ($vOH$), 1770 ($vC=O$), 1655 ($vC=O$), 1570-1590 ($vC=C$).

MS (electrospray, m/z): 381.1 ($M^+$).

Elemental Microanalysis:

|  | % C | % H | % N |
|---|---|---|---|
| Calculated: | 72.17 | 4.29 | 3.51 |
| Found: | 72.37 | 4.37 | 3.55 |

EXAMPLE 3

3-(6-Methoxy-4-oxo-4H-1-benzopyran-2-yl)-1-phenyl-1H-1,4-dihydroquinolin-4-one

The expected product is obtained according to the procedure described in Example 1 but replacing, in Step D, the 2-hydroxy-4-methoxyacetophenone by 2-hydroxy-5-methoxy-acetophenone.

Melting point: 265° C.

IR ($cm^{-1}$): 2830 ($vOCH_3$), 1740 ($vC=O$), 1655 ($vC=O$), 1570-1590 ($vC=C$).

MS (electrospray, m/z): 396.1 ($M^+$).

Elemental Microanalysis:

|  | % C | % H | % N |
|---|---|---|---|
| Calculated: | 72.63 | 4.63 | 3.39 |
| Found: | 72.74 | 4.46 | 3.36 |

EXAMPLE 4

3-(5-Methoxy-4-oxo-4H-1-benzopyran-2-yl)-1-phenyl-1H-1,4-dihydroquinolin-4-one

The expected product is obtained according to the procedure described in Example 1 but replacing, in Step D, the 2-hydroxy-4-methoxyacetophenone by 2-hydroxy-6-methoxy-acetophenone.

Melting point: 271° C.

IR ($cm^{-1}$): 2830 ($vOCH_3$), 1744 ($vC=O$), 1655 ($vC=O$), 1570-1590 ($vC=C$).

MS (electrospray, m/z): 3961 ($M^+$).

Elemental Microanalysis:

|  | % C | % H | % N |
|---|---|---|---|
| Calculated: | 72.63 | 4.63 | 3.39 |
| Found: | 72.46 | 4.57 | 3.27 |

EXAMPLE 5

3-(5,7-Dimethoxy-4-oxo-4H-1-benzopyran-2-yl)-1-phenyl-1H-1,4-dihydroquinolin-4-one Step A: 2,4-Dimethoxy-6-hydroxyacetophenone 14.5 mmol of $K_2CO_3$ are added, all at once, to 10 mmol of phloroacetophenone monohydrate dissolved in acetone. Under an inert atmosphere, 20 mmol of dimethyl sulphate are then added over a period of 30 minutes and the reaction mixture is heated at reflux of the acetone for 12 hours. After returning to ambient temperature, the mixture is poured into water to yield a white suspension which is then filtered. The white powder obtained is washed and is then recrystallised from methanol to yield the expected product.

Melting point: 80-81° C. (methanol).

Step B: 3-(5,7-Dimethoxy-4-oxo-4H-1-benzopyran-2-yl)-1-phenyl-1H-1,4-dihydroquinolin-4-one The expected product is obtained according to the procedure described in Example 1 but replacing, in Step D, the 2-hydroxy-4-methoxyacetophenone by the compound obtained in Step A above.

Melting Point: 282° C.

IR ($cm^{-1}$): 2825 ($vOCH_3$), 1744 (vC=O), 1655 (vC=O), 1570-1590 (vC=C).

MS (electrospray, m/z): 425.45 ($M^+$).

Elemental Microanalysis:

|  | % C | % H | % N |
|---|---|---|---|
| Calculated: | 70.42 | 4.77 | 3.16 |
| Found: | 70.33 | 4.76 | 3.26 |

EXAMPLE 6

3-(5-Hydroxy-4-oxo-4H-1-benzopyran-2-yl)-1-phenyl-1H-quinolin-4-one

The expected product is obtained according to the procedure described in Example 2, starting from the compound of Example 4.

Melting point: >300° C. (acetone)

IR ($cm^{-1}$): 3200 (vOH), 1770 (vC=O), 1635 (vC=O), 1570-1590 (vC=C).

MS (electrospray, m/z): 381.1 ($M^+$).

Elemental Microanalysis:

|  | % C | % H | % N |
|---|---|---|---|
| Calculated: | 72.17 | 4.29 | 3.51 |
| Found: | 72.33 | 4.40 | 3.65 |

EXAMPLE 7

3-(5-Hydroxy-7-methoxy-4-oxo-4H-1-benzopyran-2-yl)-1-phenyl-1H-quinolin-4-one 11 mmol of $BBr_3$ (as a 1M solution in dichloromethane) are added over 15 minutes, under an inert atmosphere and protected from light, to 10 mmol of the compound of Example 5 as a suspension in dichloromethane, resulting in the formation of a yellow precipitate. The reaction mixture is stirred vigorously at ambient temperature for 6 hours and is then cooled to 0° C. Ethanol is then added and the solution is concentrated in vacuo. The residue obtained is then poured into an aqueous alcoholic solution (50%) and the mixture is then vigorously stirred for 10 minutes. The precipitate obtained is filtered off and rinsed with water and then with diethyl ether to yield, after recrystallisation, the expected product in the form of a beige powder.

Melting point: 295-296° C. (acetone)

IR ($cm^{-1}$): 3224 (vOH), 1780 (vC=O), 1655 (vC=O), 1570-1590 (vC=C).

MS (electrospray, m/z): 411.41 ($M^+$).

Elemental Microanalysis:

|  | % C | % H | % N |
|---|---|---|---|
| Calculated: | 72.99 | 4.16 | 3.40 |
| Found: | 72.70 | 4.10 | 3.45 |

EXAMPLE 8

3-(4-Oxo-4H-1-benzopyran-2-yl)-1-phenyl-1H-quinolin-4-one

The expected product is obtained according to the procedure described in Example 1 but replacing, in Step D, the 2-hydroxy-4-methoxyacetophenone by acetophenone.

Melting point: 327-328° C.

MS (electrospray, m/z): 365.4 ($M^+$).

Elemental Microanalysis

|  | % C | % H | % N |
|---|---|---|---|
| Calculated: | 78.89 | 4.14 | 3.83 |
| Found: | 78.60 | 4.10 | 3.60 |

EXAMPLE 9

3-[5,7-Dimethoxy-8-(1-methyl-1,2,5,6-tetrahydropyridin-4-yl)-4-oxo-4H-1-benzopyran-2-yl]-1-phenyl-1H-1,4-dihydroquinolin-4-one Step A: 4-(2,4-Dimethoxy-6-hydroxy-5-methylcarbonylphenyl)-1-methyl-1,2,5,6-tetrahydropyridine To 10 mmol of the compound obtained in Step A of Example 5, dissolved in glacial acetic acid, there are added, slowly so as not to exceed 25° C., 11.5 mmol of 1-methylpiperidin-4-one. When the addition is complete, a stream of hydrogen chloride gas is bubbled through for 1 hour 40 minutes, and the reaction mixture is then heated at a temperature between 95 and 100° C. for 5 hours. The acetic acid is removed by distillation in vacuo, and the residual oil is then taken up in water and extracted with diethyl ether. The aqueous phase is made basic by adding 40% NaOH solution. The precipitate obtained is filtered off, rinsed with copious amounts of water and recrystallised from petroleum ether to yield the expected product.

Melting point: 143-144° C.

IR (KBr, cm$^{-1}$): 3400-3200 (vOH), 2843 (vOCH$_3$), 1680 (vC=O), 1655 (vC=C).

MS (EI, m/z): 291 (M$^+$).

Step B: 3-[5,7-Dimethoxy-8-(1-methyl-1,2,5,6-tetrahydropyridinyl)-4-oxo-4H-1-benzopyran-2-yl]-1-phenyl-1-H-1,4-dihydroquinolin-4-one The expected product is obtained according to the procedure described in Example 1 but replacing, in Step D, the 2-hydroxy-4-methoxyacetophenone by the compound obtained in Step A above.

Melting point: 248-250° C. (acetone).

IR (cm$^{-1}$): 2835 (vOCH$_3$), 1755 (vC=O), 1675 (vC=O), 1570-1590 (vC=C).

MS (electrospray, m/z): 520.6 (M$^+$).

Elemental Microanalysis:

|  | % C | % H | % N |
| --- | --- | --- | --- |
| Calculated: | 73.28 | 5.10 | 5.22 |
| Found: | 73.83 | 5.42 | 5.38 |

EXAMPLE 10

3-(5,7-Dihydroxy-4-oxo-4H-1-benzopyran-2-yl)-1-phenyl-1H-1,4-dihydroquinolin-4-one The expected product is obtained according to the procedure described in Example 2, starting from the compound of Example 5.

Melting point: 365-368° C. (acetone).

IR (cm$^{-1}$): 3224 (vOH), 1780 (vC=O), 1655 (vC=O), 1570-1590 (vC=C).

MS (electrospray, m/z): 397.4 (M$^+$).

Elemental Microanalysis:

|  | % C | % H | % N |
| --- | --- | --- | --- |
| Calculated: | 72.54 | 3.80 | 3.52 |
| Found: | 72.20 | 4.01 | 3.33 |

EXAMPLE 11

Ethyl [2-(4-oxo-1-phenyl-1H-1,4-dihydroquinolin-3-yl)-4H-1-benzopyran-7-yloxy]acetate To 10 mmol of the compound of Example 2, suspended in acetone, there are slowly added 20 mmol of potassium carbonate and then 20 mmol of ethyl bromoacetate. The mixture is heated at reflux of the solvent for 2 hours 30 minutes and then, after returning to ambient temperature, is poured into water. The insoluble material obtained is filtered off and rinsed with copious amounts of water to yield the expected product in the form of a white solid.

Melting point: 330° C.

IR (cm$^{-1}$): 1744 (vC=O), 1680 (vC=O), 1655 (vC=O), 1570-1590 (vC=C).

MS (electrospray, m/z 467.48 (M$^+$).

Elemental Microanalysis:

|  | % C | % H | % N |
| --- | --- | --- | --- |
| Calculated: | 71.94 | 4.53 | 3.00 |
| Found: | 71.70 | 4.77 | 3.40 |

EXAMPLE 12

3-[5,7-Dimethoxy-8-(1-methyl-1,2,5,6-tetrahydropyridin-4-yl)-4-oxo-4H-1-benzopyran-2-yl]-1-methyl-1H-1,4-dihydroquinolin-4-one Step A: Diethyl N-phenylaminomethylenemalonate The expected product is obtained according to the procedure described in Step A of Example 1, but replacing the diphenylamine by aniline.

Melting point: 46-48° C. (hexane).

MS (EI, m/z): 263 (M$^+$).

Step B: Diethyl N-methyl-N-phenylaminomethylenemalonate

To 10 mmol of the compound obtained in the previous Step, dissolved in tetrahydrofuran, there are added, slowly (in small portions) and under an inert atmosphere, 12 mmol of 95% NaH and then, dropwise, 30 mmol of iodomethane. The reaction mixture is then stirred, at ambient temperature and under an inert atmosphere, for 12 hours. 1 mL of methanol is added in order to neutralise the excess of sodium hydride. The solution is then concentrated in vacuo, and then water is added to the residual oil obtained. After extraction with dichloromethane, the combined organic phases are dried, filtered and concentrated under reduced pressure to yield the expected product in the form of a colourless oil.

MS (EI, m/z): 276 (M$^+$).

Step C: 3-[5,7-Dimethoxy-8-(1-methyl-1,2,5,6-tetrahydropyridin-4-yl)-4-oxo-4H-1-benzopyran-2-yl]-1-methyl-1H-1,4-dihydroquinolin-4-one The expected product is obtained according to the procedure described in Steps B to F of Example 1 but replacing, in Step B, the compound obtained in Step A of Example 1 by the compound obtained in Step B above and replacing, in Step D, the 2-hydroxy-4-methoxyacetophenone by the compound obtained in Step A of Example 9.

Melting point: 289-291° C. (acetone).

IR (cm$^{-1}$): 2835 (vOCH$_3$), 1755 (vC=O), 1675 (vC=), 1570-1590 (vC=C).

MS (electrospray, m/z): 458.5 (M$^+$).

Elemental Microanalysis:

|  | % C | % H | % N |
|---|---|---|---|
| Calculated: | 70.73 | 5.72 | 6.11 |
| Found: | 70.25 | 5.48 | 5.78 |

EXAMPLE 13

3-[5,7-Dimethoxy-8-[1-(4-fluorobenzyl)-1,2,5,6-tetrahydropyridin-4-yl]-4-oxo-4H-1-benzopyran-2-yl]-1-phenyl-1H-1,4-dihydroquinolin-4-one Step A: 1-(4-Fluorobenzyl)piperidin-4-one:

To 10 mmol of piperidin-4-one hydrochloride monohydrate and 20 mmol of triethylamine, dissolved in dichloromethane, there are slowly added 10 mmol of 4-fluorobenzyl chloride; the reaction mixture is then heated at reflux of the solvent for 48 hours, with vigorous stirring. After returning to ambient temperature, water is added and then, after separation of the phases, the organic phase is dried, filtered and concentrated in vacuo to yield the expected product in the form of an orange oil.

MS (EI, m/z): 207.2 (M$^+$).

Step B: 4-(3-Acetyl-4,6-dimethoxy-2-hydroxyphenyl-1]-(4-fluorobenzyl)-1,2,5,6-tetrahydropyridine To 10 mmol of the compound obtained in Step A of Example 5, dissolved in glacial acetic acid, there are added, slowly so as not to exceed 25° C., 11 mmol of the compound obtained in Step A above. When the addition is complete, a stream of hydrogen chloride is passed through the solution for 2 hours, and the reaction mixture is then heated at a temperature between 95 and 100° C. for 5 hours. The acetic acid is removed by distillation in vacuo, and then water is added to the residual oil obtained. After extraction with diethyl ether, the aqueous phase is made basic using 40% NaOH solution. The precipitate obtained is filtered off, rinsed with copious amounts of water and recrystallised from a mixture of ether/ethyl acetate (90/10) to yield the expected product in the form of a beige solid.

Melting point: 147-150° C.

IR (KBr, cm$^{-1}$): 3400-3200 (vOH), 2871 (vCH of OCH$_3$), 1633 (vC=O), 1655 (vC=C), 1350-1100 (vC—F).

MS (EI, m/z): 385.4 (M$^+$).

Step C: 3-[5,7-Dimethoxy-8-[1-(4-fluorobenzyl)-1,2,5,6-tetrahydropyridin-4-yl]-4-oxo-4H-1-benzopyran-2-yl]-1-phenyl-1H-1,4-dihydroquinolin-4-one The expected product is obtained according to the procedure described in Example 1, but replacing, in Step D, the 2-hydroxy-4-methoxyacetophenone by the compound obtained in Step B above.

Melting point: 218-219° C. (acetone).

IR (cm$^{-1}$): 2835 (vOCH$_3$), 1755 (vC=O), 1655 (vC=O), 1570-1590 (vC=C).

MS (electrospray, m/z): 614.66 (M$^+$).

EXAMPLE 14

3-[5,7-Dihydroxy-8-(1-methyl-1,2,5,6-tetrahydropyridin-4-yl)$_4$-oxo-4H-1-benzopyran-2-yl]-1-phenyl-1H-1,4-dihydroquinolin-4-one 10 mmol of the compound of Example 9 are dispersed in pyridinium chloride; the mixture is then heated at 180° C., in a sealed tube, for 12 hours. After cooling to 100° C., the reaction mixture is then poured into water and the pH is adjusted to 7-8 using 10% sodium hydrogen carbonate solution (the pH is initially 1). The insoluble material is separated off by filtration and rinsed with water to yield the expected product.

Melting point: >250° C.

IR (cm$^{-1}$): 3330 (vOH), 1785 (vC=O), 1665 (vC=O), 1570-1590 (vC=C).

MS (electrospray, m/z): 492.5 (M$^+$).

Elemental Microanalysis:

|  | % C | % H | % N |
|---|---|---|---|
| Calculated: | 72.94 | 5.12 | 5.87 |
| Found: | 73.16 | 4.91 | 5.69 |

EXAMPLE 15

3-[5,7-Dimethoxy-8-(1-benzyl-1,2,5,6-tetrahydropyridin-4-yl)-4-oxo-4H-1-benzopyran-2-yl]-1-phenyl-1H-1,4-dihydroquinolin-4-one The expected product is obtained according to the procedure described in Examples B to C of Example 13 but replacing, in Step B, the compound obtained in Step A of Example 13 by 1-benzylpiperidin-4-one.

Melting point: 248-249° C. (acetone).

IR (cm$^{-1}$): 2830 (vCH of OCH$_3$), 1765 (vC=O), 1655 (vC=O), 1570-1590 (vC=C),

MS (electrospray, m/z): 596.9 (M$^+$).

Elemental Microanalysis:

|  | % C | % H | % N |
|---|---|---|---|
| Calculated: | 76.49 | 5.41 | 4.69 |
| Found: | 76.06 | 5.03 | 4.93 |

EXAMPLE 16

3-[5,7-Dihydroxy-8-(1-benzyl-1,2,5,6-tetrahydropyridin-4-yl)-4-oxo-4H-1-benzopyran-2-yl]-1-phenyl-1H-1,4-dihydroquinolin-4-one The expected product is obtained according to the procedure described in Example 14, starting from the compound of Example 15.

Melting point: 230-231° C. (acetone).

IR (cm$^{-1}$): 3340 (vOH), 1752 (vC=O), 1655 (vC=O), 1570-1590 (vC=C).

MS (electrospray, m/z): 568.6 (M$^+$).

Elemental Microanalysis:

|  | % C | % H | % N |
|---|---|---|---|
| Calculated: | 76.04 | 4.96 | 4.93 |
| Found: | 76.39 | 5.41 | 5.22 |

EXAMPLE 17

3-[5,7-Dihydroxy-8-[1-(4-fluorobenzyl)-1,2,5,6-tetrahydropyridin-4-yl]-4-oxo-4H-1-benzopyran-2-yl]-1-phenyl-1H-1,4-dihydroquinolin-4-one The expected product is obtained according to the procedure described in Example 14, starting from the compound of Example 13.
Melting point: 197-198° C. (acetone).
IR (cm$^{-1}$): 3245 (vOH), 1775 (vC=O), 1655 (vC=O), 1570-1590 (vC=C).
MS (electrospray, m/z): 586.6 (M$^+$).

Elemental Microanalysis:

|  | % C | % H | % N |
|---|---|---|---|
| Calculated: | 73.71 | 4.64 | 4.78 |
| Found: | 73.20 | 4.28 | 4.34 |

EXAMPLE 18

3-[5,7-Dimethoxy-8-[1-(4-methoxybenzyl)-1,2,5,6-tetrahydropyridin-4-yl]-4-oxo-4H-1-benzopyran-2-yl]-1-phenyl-1H-1,4-dihydro-quinolin-4-one The expected product is obtained according to the procedure described in Example 13 but replacing, in Step A, the 4-fluorobenzyl chloride by 4-methoxybenzyl chloride.
Melting point: 232-235° C. (acetone).
IR (cm$^{-1}$): 2845 (vOCH$_3$), 1750 (vC=O), 1655 (vC=O), 1570-1590 (vC=C).
MS (electrospray, m/z): 626.7 (M$^+$).

EXAMPLE 19

3-[5,7-Dimethoxy-8-(1,2,5,6-tetrahydropyridin-4-yl)-4-oxo-4H-1-benzopyran-2-yl]-1-phenyl-1H-1,4-dihydroquinolin-4-one To 10 mmol of the compound of Example 18 suspended in glacial acetic acid there is added, under an inert atmosphere, 0.9 mg of Pd/C (10% by weight). The reaction mixture is heated at 70° C. and stirred under an atmosphere of hydrogen at atmospheric pressure for 5 hours. The reaction mixture is then filtered over Celite and then washed with methanol. The solvents are removed by distillation in vacuo. Water pH-adjusted to 8-9 is added to the residue obtained. Extraction with the mixture CH$_2$Cl$_2$/MeOH (90/10) yields the expected product in the form of a white solid.
Melting point: 251-253° C. (diethyl ether/acetone).
IR (cm$^{-1}$): 3387 (vN—H), 2880 (vOCH$_3$), 1780 (vC=O), 1655 (vC=O), 1570-1590 (vC=C).
MS (electrospray, m/z): 506.5 (M$^+$).

Elemental Microanalysis:

|  | % C | % H | % N |
|---|---|---|---|
| Calculated: | 73.50 | 5.17 | 5.53 |
| Found: | 73.12 | 5.58 | 4.98 |

EXAMPLE 20

3-[5,7-Dimethoxy-8-(1-isopropyl-1,2,5,6-tetrahydropyridinyl)-4-oxo-4H-1-benzopyran-2-yl]-1-phenyl-1H-1,4-dihydroquinolin-4-one The expected product is obtained according to the procedure described in Examples B to C of Example 13 but replacing, in Step B, the compound obtained in Step A of Example 13 by N-isopropylpiperidin-4-one.
Melting point: 248-249° C. (acetone).
IR (cm$^{-1}$): 2850 (vOCH$_3$), 1755 (vC=O), 1650 (vC=O), 1570-1590 (vC=C).
MS (electrospray, m/z): 548.6 (M$^+$).

Elemental Microanalysis

|  | % C | % H | % N |
|---|---|---|---|
| Calculated: | 74.43 | 5.88 | 5.11 |
| Found: | 73.78 | 5.23 | 5.78 |

EXAMPLE 21

3-[7-(4-Bromobenzyloxy)-4-oxo-4H-1-benzopyran-2-yl]-1-phenyl-1H-quinolin-4-one

The expected product is obtained according to the procedure described in Example 11, starting from the compound of Example 2 but replacing the ethyl bromoacetate by 4-bromobenzyl chloride.
IR (cm$^{-1}$): 1744 (vC=O), 1655 (vC=O), 1570-1590 (vC=C).
MS (electrospray, m/z): 549.4 (M$^+$).

Elemental Microanalysis:

|  | % C | % H | % N |
|---|---|---|---|
| Calculated: | 67.65 | 3.66 | 2.54 |
| Found: | 66.95 | 4.21 | 2.44 |

EXAMPLE 22

3-[5,7-Dimethoxy-8-[1-(2-dimethylaminoethyl)-1,2,5,6-tetrahydro-pyridin-4-yl]-4-oxo-4H-1-benzopyran-2-yl]-1-phenyl-1H-1,4-dihydroquinolin-4-one The expected product is obtained according to the procedure described in Example 13 but replacing, in Step A, the 4-fluorobenzyl chloride by 2-chloro-N,N-dimethylethylamine.

EXAMPLE 23

3-[5,7-Dihydroxy-8-[1-(2-dimethylaminoethyl)-1,2,5,6-tetrahydro-pyridin-4-yl]-4-oxo-4H-1-benzopyran-2-yl]-1-phenyl-1H-1,4-dihydroquinolin-4-one The expected product is obtained according to the procedure described in Example 2, starting from the compound of Example 22.

PHARMACOLOGICAL STUDY OF COMPOUND OF THE INVENTION

EXAMPLE 24

In Vitro Study of the Cytotoxicity Due to Compounds of the Invention

Eleven cell lines from cancers of different origins and sites (lung, breast, prostate, colon, blood, bladder, skin, ovary, brain) are cultured in order to study the various compounds in comparison to the reference substance.

The cells are incubated for 96 hours with various concentrations of compounds of the invention.

The in vitro cytotoxic activity is determined by the MTT [3-(4,5-dimethylthiazol-2-yl)-2,5-diphenyltetrazolium bromide] test as described by Carmichael in Cancer Res.—1987; 47 (4): 936-942.

The activity is expressed in terms of the $IC_{50}$, that is to say the concentration which inhibits proliferation of the tumour cells by 50%.

In this model, the compounds of the invention have an intrinsic cytotoxic activity with respect to one or more tumour cell lines.

By way of example, the compound of Example 9 has cytotoxic activity with respect to 8 of the 11 lines tested ($IC_{50}$ values of from 2 to 10 µM depending on the cell line used).

The compound of Example 14 has $IC_{50}$ values of from 0.05 to 0.25 µM with respect to 5 of the 11 lines tested.

EXAMPLE 25

Synergistic Effect, In Vitro, of Compounds of the Invention in Combination with Known Anti-Cancer Agents Three cell lines which are sensitive to three anti-cancer agents are used: breast cancer cells in association with treatment with tamoxifen (TXL), lung cancer cells in association with treatment with cisplatin (CDDP), and colon cancer cells in association with treatment with SN38, a metabolite of CPT-11 (irinotecan).

The tumour cells are incubated for 96 hours together with five different concentrations of each of the compounds of the invention and five concentrations of each of the anti-cancer agents in association.

The in vitro cytotoxic activity is determined by the MTT test described in Example 24. Analysis of the data is carried out according to the method of Chou and Talabay, published in Trends Pharmaceutical Sci.—1983; 4:450.

The compounds of the invention show a synergistic effect with the different anti-cancer agents tested, that is to say they reinforce the cytotoxic activity of the anti-cancer agent administered simultaneously.

By way of example, the compounds of Examples 14 and 16 show a synergistic effect both with paclitaxel and with cisplatin.

EXAMPLE 26

Apoptotic Effect of Compounds of the Invention

Apoptosis is a natural mechanism which allows the human body to rid itself of abnormal cells such as cancerous cells.

Study of the pro-apoptotic effects of compounds of the invention is carried out on a prostate cancer line (LN CaP). The cells were incubated for periods ranging from 8 to 96 hours at the $IC_{50}$ concentration.

The TUNEL test was then carried out according to the method described by Sgonc in Trends Genetics—1994; 10:41.

The compounds of the invention are capable of bringing about apoptosis, the maximum intensity of which occurs at different times depending on the compounds.

The compounds of the invention differ from previously described substances in their ability to bring about apoptosis earlier. By way of example, very high apoptosis is brought about early (8 hours) by the compound of Example 6.

EXAMPLE 27

Pharmaceutical Composition

Preparation formula for 1000 tablets each containing 10 mg of active ingredient

| | |
|---|---|
| Compound of Example 9 | 10 g |
| Hydroxypropyl cellulose | 2 g |
| Wheat starch | 10 g |
| Lactose | 100 g |
| Magnesium stearate | 3 g |
| Talc | 3 g |

The invention claimed is:
1. A compound selcted from those of formula (I):

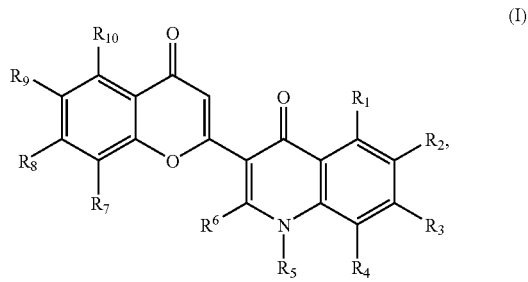

wherein:

$R_1$, $R_2$, $R_3$, $R_4$, $R_6$, $R_8$, $R_9$ and $R_{10}$, which may be the same or different, each represent a group selected from hydrogen, hydroxy, linear or branched ($C_1$-$C_6$)alkoxy, linear or branched ($C_1$-$C_6$)alkyl, arylalkoxy in which the alkoxy group is linear or branched ($C_1$-$C_6$), alkoxycarbonylalkoxy in which each of the alkoxy groups is linear or branched ($C_1$-$C_6$), and OR' wherein R' represents an a phosphate group —PH(OH)$_2$, a sulfate group —SO$_3$H, carboxyalkylcarbonyl in which the alkyl group is linear or branched ($C_{1-6}$), dialkylaminoalkyl-carbonyl in which each of the alkyl groups is linear or branched ($C_{1-6}$), or carboxyalkylaminocarbonyl in which the alkyl group is linear or branched (C $C_{1-6}$), $R_5$ represents a group selected from linear or branched ($C_1$-$C_6$)alkyl, aryl and heteroaryl, $R_7$ represents a group selected from hydrogen, hydroxy, linear or branched ($C_1$-$C_6$)alkoxy, linear or branched ($C_1$-$C_6$)alkyl and ($C_3$-$C_7$)cycloalkyl, or $R_7$ represents a nitrogen-containing or oxygen-containing heterocycle, its optical isomers thereof, addition salts thereof with a pharmaceutically acceptable acid or base, thereof, it being understood that:

an aryl group may be phenyl, biphenylyl, naphthyl or tetrahydronaphthyl, each of those groups being optionally substituted by one or more identical or different atoms or groups selected from halogen, linear or branched ($C_1$-$C_6$)alkyl, hydroxy, linear or branched ($C_1$-$C_6$)alkoxy, linear or branched ($C_1$-$C_6$)polyhaloalkyl, amino (optionally substituted by one or two linear or branched ($C_1$-$C_6$)alkyl), nitro and ($C_1$-$C_2$)alkylenedioxy, a heteroaryl group may be a 5- to 12-membered group which either is monocyclic and aromatic or is bicyclic with at least one of the rings being of aromatic character and which contains one, two or three hetero atoms selected from oxygen, nitrogen and sulphur, it being understood that the heteroaryl group may be optionally substituted by one or more identical or different atoms or groups selected from halogen, linear or branched ($C_1$-$C_6$)alkyl, hydroxy, linear or branched ($C_1$-$C_6$) alkoxy, linear or branched ($C_1$-$C_6$)polyhaloalkyl and amino (optionally substituted by one or two linear or branched ($C_1$-$C_6$)alkyl), a nitrogen-containing heterocycle may be a saturated or unsaturated, 5- to 7-membered monocyclic group containing a nitrogen atom and optionally substituted by one or more groups selected from hydroxy, linear or branched ($C_1$-$C_6$)alkoxy, linear or branched ($C_1$-$C_6$) alkyl, aryl-($C_1$-$C_6$)alkyl in which the alkyl moiety is linear or branched and amino-($C_1$-$C_6$)alkyl in which the alkyl moiety is linear or branched and in which the amino group is optionally substituted by one or two linear or branched ($C_1$-$C_6$)alkyl, an oxygen-containing heterocycle may be a saturated or unsaturated, 5- to 7-membered monocyclic group containing an oxygen atom and optionally substituted by one or more groups selected from hydroxy, linear or branched ($C_1$-$C_6$)alkoxy, linear or branched ($C_1$-$C_6$) alkyl, aryl-($C_1$-$C_6$)alkyl in which the alkyl moiety is linear or branched and amino-($C_1$-$C_6$)alkyl in which the alkyl moiety is linear or branched and in which the amino group is optionally substituted by one or two linear or branched ($C_1$-$C_6$)alkyl.

2. A compound of claim 1, wherein $R_1$, $R_2$, $R_3$, $R_4$, $R_6$, $R_8$, $R_9$, and $R_{10}$, which may be the same or different, each represent a group selected from hydrogen, hydroxy, linear or branched ($C_1$-$C_6$)alkoxy, linear or branched ($C_1$-$C_6$)alkyl, arylalkoxy in which the alkoxy group is linear or branched ($C_1$-$C_6$) and alkoxycarbonylalkoxy in which each of the alkoxy groups is linear or branched ($C_1$-$C_6$).

3. A compound of claim 1, wherein $R_1$, $R_2$, $R_3$, $R_4$, $R_6$, $R_8$, $R_9$ and $R_{10}$, which may be the same or different, each represent a group selected from hydrogen, hydroxy, linear or branched ($C_1$-$C_6$)alkoxy, linear or branched ($C_1$-$C_6$)alkyl, arylalkoxy in which the alkoxy group is linear or branched ($C_1$-$C_6$), alkoxycarbonylalkoxy in which each of the alkoxy groups is linear or branched ($C_1$-$C_6$), and OR' in which R' represents a group selected from phosphate—PO(OH)$_2$, sulfate—SO$_3$H, carboxyalkylcarbonyl in which the alkyl group is linear or branched ($C_1$-$C_6$), dialkylaminoalkylcarbonyl in which each of the alkyl groups is linear or branched ($C_1$-$C_6$), and carboxyalkylaminocarbonyl in which the alkyl group is linear or branched ($C_1$-$C_6$).

4. A compound of claim 1, wherein $R_5$ represents aryl.

5. A compound of claim 1, wherein $R_7$ represents hydrogen.

6. A compound of claim 1, wherein $R_7$ represents an optionally substituted nitrogen-containing heterocycle.

7. A compound of claim 1, wherein $R_5$ represents phenyl and $R_7$ represents hydrogen or substituted 1,2,3,6-tetrahydro-4-pyridyl.

8. A compound of claim 1, which is 3-(5-hydroxy-4-oxo-4H-1-benzopyran-2 -yl)-1-phenyl-1H-quinolin-4-one.

9. A compound of claim 1, which is 3-[5,7-dimethoxy-8-(1-methyl-1,2,5,6-tetrahydropyridin-4-yl)-4-oxo-4-benzopyran-2-yl]-1-phenyl-1H-1,4-dihydroquinolin-4-one.

10. A compound of claim 1, which is 3-(5,7-dihydroxy-4-oxo-4H-1-benzopyran-2-yl)-1-phenyl-1H-1,4-dihydroquinolin-4-one.

11. A compound of claim 1, which is 3-[5,7-dihydroxy-8-(1-methyl-1,2,5,6-tetrahydropyridin-4-yl)-4-oxo-4H-1-benzopyran-2-yl]-1-phenyl-1H-1,4-dihydroquinolin-4-one.

12. A pharmaceutical composition comprising as active ingredient a compound of claim 1, in combination with one or more inert, non-toxic, pharmaceutically acceptable carriers.

* * * * *

UNITED STATES PATENT AND TRADEMARK OFFICE
CERTIFICATE OF CORRECTION

| | | |
|---|---|---|
| PATENT NO. | : 7,339,061 B2 | Page 1 of 1 |
| APPLICATION NO. | : 10/519208 | |
| DATED | : March 4, 2008 | |
| INVENTOR(S) | : Jean-Daniel Brion et al. | |

It is certified that error appears in the above-identified patent and that said Letters Patent is hereby corrected as shown below:

Column 18, Line 66:  Delete "an"

Column 20, Line 36:  "-4-oxo-4-" Should be "-4-oxo-4$H$-1-"

Signed and Sealed this

Twenty-first Day of April, 2009

JOHN DOLL
*Acting Director of the United States Patent and Trademark Office*